(12) United States Patent
Stafford

(10) Patent No.: US 10,576,259 B2
(45) Date of Patent: Mar. 3, 2020

(54) CLAMP FOR RETAINING AN IV TUBE

(71) Applicant: HMJ Medical LLC, Hastings, MI (US)

(72) Inventor: Drew Stafford, Hastings, MI (US)

(73) Assignee: HMJ Medical LLC, Hastings, MI (US)

( * ) Notice: Subject to any disclaimer, the term of this patent is extended or adjusted under 35 U.S.C. 154(b) by 0 days.

(21) Appl. No.: 16/356,337

(22) Filed: Mar. 18, 2019

(65) Prior Publication Data

US 2019/0282793 A1    Sep. 19, 2019

Related U.S. Application Data

(60) Provisional application No. 62/644,524, filed on Mar. 18, 2018.

(51) Int. Cl.
  *F16B 2/20*   (2006.01)
  *F16B 7/04*   (2006.01)
  *A61M 39/08*  (2006.01)

(52) U.S. Cl.
  CPC ....... *A61M 39/08* (2013.01); *A61M 2039/087* (2013.01)

(58) Field of Classification Search
  CPC ............ A61M 39/08; A61M 2039/087; A61M 5/1411; F16B 2/06; F16B 2/08; F16B 2/10; F16B 2/20; F16B 7/04; Y10T 24/14; Y10T 24/1402; Y10T 24/1471; Y10T 24/15; Y10T 24/44034; Y10T 24/44291; Y10T 24/44427; Y10T 24/44444; Y10T 24/44453; A61B 17/122
  USPC ........ 248/74.2, 74.4, 74.1; 24/489, 495, 496
  See application file for complete search history.

(56) References Cited

U.S. PATENT DOCUMENTS

| | | | |
|---|---|---|---|
| 4,340,052 A | | 7/1982 | Dennehey et al. |
| 4,405,312 A | | 9/1983 | Gross et al. |
| 5,423,501 A | * | 6/1995 | Yu .......................... A01G 17/08 248/61 |
| 5,703,330 A | * | 12/1997 | Kujawski ............ B60R 16/0215 138/157 |
| 5,755,225 A | | 5/1998 | Hutson |
| 8,294,583 B2 | | 10/2012 | Sayegh et al. |
| 9,004,545 B2 | | 4/2015 | Whitaker et al. |
| 2005/0038453 A1 | | 2/2005 | Raulerson |
| 2008/0082079 A1 | | 4/2008 | Braga et al. |
| 2010/0222793 A1 | | 9/2010 | Skipper |
| 2014/0324024 A1 | | 10/2014 | Tejani |
| 2017/0049956 A1 | * | 2/2017 | Kitchen .................... F16B 2/10 |

* cited by examiner

*Primary Examiner* — Jack W Lavinder
(74) *Attorney, Agent, or Firm* — Oppenhuizen Law PLC; David L. Oppenhuizen

(57) ABSTRACT

A clamp for retaining an IV tube having a pair of clamp sections configured to be selectively secured together. Each clamp section includes a semi-cylindrical surface, and the semi-cylindrical surfaces are positioned to mirror one another when the clamp sections are secured together to frictionally engage around the IV tube. Each clamp section has a finger grip on an outer surface which is positioned on an opposite side of the clamp section from the semi-cylindrical surface. Each finger grip also has an arched surface which includes a medial portion positioned between each end of the finger grips, and at least one end of the finger grip flares away from the semi-cylindrical surface. The finger grip can have a finger shield which extends laterally beyond the semi-cylindrical surface. At least one of the finger grips may be symmetrical.

15 Claims, 7 Drawing Sheets

CLAMP FOR RETAINING AN IV TUBE

CROSS REFERENCE TO RELATED APPLICATION

This application claims the benefit of U.S. Provisional Application 62/644,524, which was filed on Mar. 18, 2018, the entire disclosure of which is hereby incorporated by reference.

BACKGROUND OF THE INVENTION

1. Field of the Invention

The present invention pertains to a clamp for retaining an IV tube. More particularly, the present invention pertains to a handheld clamp for retaining an IV tube connected to a fluid-filled IV bag to assist a medical provider with grasping and safely piercing a sealed end of the IV tube with an IV spike.

2. Description of the Prior Art

Fluid-filled IV bags are well known and commonly used throughout the medical field. It is widely known that medical patients who need to receive fluids intravenously will have an intravenous connection established with his or her body, such as through a peripheral line that accesses the body through the arms, hands, legs, or feet, or through a central line that has an access point on the patient's torso. A sterile section of IV tubing is used to connect the intravenous connection on the patient's body with the fluid-filled IV bag.

The IV bag typically has at least one tubing port at the bottom of the bag. The tubing port is a shortened section of tubing which has a first end that is connected to the IV bag, and a second free end that is sealed with a membrane to contain the fluid within the IV bag.

A specific procedure is followed by a medical provider when the tubing port is connected to an IV tube, which in turn is connected on the opposite end thereof to the intravenous connection on the patient. The end of the IV tube includes an IV spike, which is well-known to those having ordinary skill in the art as essentially being an enlarged needle, or spike, that is inserted partially into the tubing port and forcibly pierces through the membrane to allow the fluid within the IV bag to flow downwardly through the tubing port and through the IV tube to the intravenous connection on the patient.

In doing so, it is critical that the IV spike and the tubing port remain sterile and are not permitted to touch anything until the connection between the two has been made. If the IV spike or tubing port do touch anything and sterility has been compromised, then the IV bag and/or the IV tube must be thrown away and replaced. In addition, there is a potential source for infection to the patient when the IV spike or tubing port accidentally touch something and are no longer sterile, but the medical provider is unaware of the possible contamination and proceeds to use the compromised items nonetheless.

Connecting the IV spike into the tubing port can be somewhat awkward and cumbersome because the medical provider must firmly grasp the pliable tubing port and then insert the IV spike directly into the end of the tubing port. Sometimes this has to occur quickly during an emergency situation, or at night when there is limited visibility. Accordingly, this particular process is prone to error. For example, the medical provider might accidentally miss inserting the IV spike into the end of the tubing port and accidentally touch the IV spike to his or her fingers holding the tubing port. In some extreme cases where the medical provider is being rushed, the IV spike may even pierce the medical provider's skin on the fingers holding the tubing port. In addition, the IV spike might be inserted into the tubing port at an askew angle, and the IV spike may actually pierce through the side wall of the tubing port rather than only through the membrane. All of these potential mistakes render the IV bag unsuitable for use, as well as potentially contaminating the IV spike.

Thus, there remains a need for a device which allows a medical provider to securely and safely grasp the tubing port on an IV bag to assist with safely inserting an IV spike therein.

There do exist in the prior art various IV clamps for retaining an IV tube in place, such as the type disclosed in U.S. Pat. No. 5,755,225 to Hutson. However, these are not suitable for addressing the problem discussed above because these clamps do not have suitable finger grips for grasping the loose end of a tubing port since they have a different specific function. This device also would not protect the medical provider's fingers from the IV spike.

The present invention, as is detailed hereinbelow, seeks to address the problems discussed above by providing a clamp for retaining an IV tube connected to a fluid-filled IV bag to assist a medical provider with piercing a sealed end of the IV tube with an IV spike.

SUMMARY OF THE INVENTION

The present invention provides a clamp for retaining an IV tube comprising:
  a pair of clamp sections that are configured to be selectively secured to one another, each clamp section includes a semi-cylindrical surface, and the semi-cylindrical surfaces are positioned to mirror one another when the clamp sections are secured to one another, wherein the semi-cylindrical surfaces cooperatively define a cylindrical void between the clamp sections, and the semi-cylindrical surfaces are configured to surround and frictionally engage with the IV tube when the clamp sections are secured to one another; and
  each clamp section has a finger grip on an outer surface of the clamp section opposite the semi-cylindrical surface, each finger grip further having an arched surface which includes a medial portion positioned between each end of the finger grips, and at least one end of the finger grip flares away from the semi-cylindrical surface.

Optionally, the clamp sections are hingedly secured to one another.

Optionally, at least one of the semi-cylindrical surfaces includes a resiliently deformable lining, such as a resilient foam lining, to help secure an IV tube held between the clamp sections.

Optionally, at least one of the semi-cylindrical surfaces includes a lining having an adhesive to help secure an IV tube held between the clamp sections.

Optionally, at least one of the semi-cylindrical surfaces has a textured surface to help secure an IV tube held between the clamp sections.

Optionally, the clamp is configured to securely engage, or lock, the clamp sections to one another. This may be accomplished by use of a latching mechanism or other hinge device which securely holds the clamp sections together once a medical provider has selectively engaged the clamp sections together.

Optionally, at least one of the finger grips is symmetrical.

Optionally, at least one of the ends of the finger grips includes a finger shield which extends laterally beyond the semi-cylindrical surfaces.

Optionally, the semi-cylindrical surface of at least one clamp section has an axis y, and the finger grip has a curved or arched surface having an axis x, wherein the axes x and y are oriented perpendicular to one another.

For a more complete understanding of the present invention, reference is made to the following detailed description and accompanying drawings. In the drawings, like reference characters refer to like parts throughout the views in which:

DETAILED DESCRIPTION OF THE PREFERRED EMBODIMENT

Figure 1:
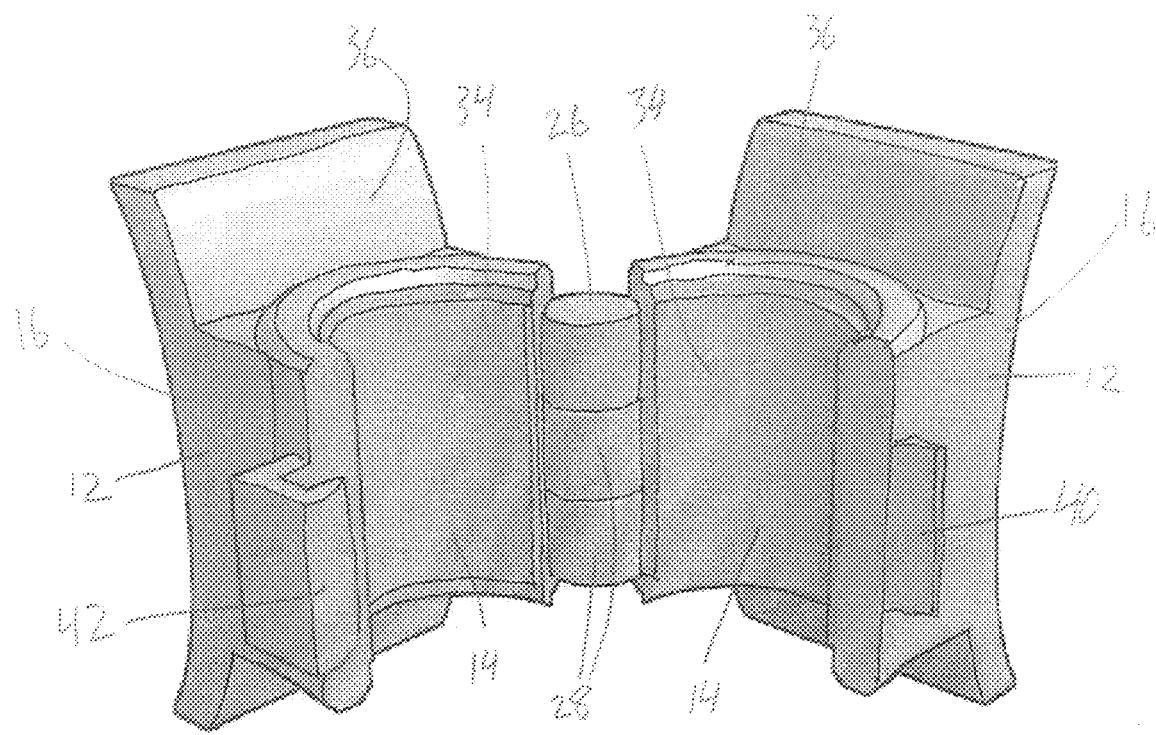
FIG. 1 is a front perspective view of a first embodiment of the present invention hereof showing the clamp sections hingedly connected together and open with respect to one another.

In accordance with the present invention, and as shown generally in FIGS. 1-6, there is provided a clamp 10 for retaining an IV tube comprising a pair of clamp sections 12 that are configured to be selectively secured to one another. Preferably, the clamp sections 12 are hingedly secured to one another. Each clamp section 12 includes a concave semi-cylindrical surface 14, and the semi-cylindrical surface 14 on each clamp section 12 is positioned to mirror one another when the clamp sections 12 are secured together to one another. When the clamp sections 12 are secured together the semi-cylindrical surfaces 14 cooperatively define a cylindrical void between the clamp sections 12 that is configured to receive the IV tube.

Figure 10:
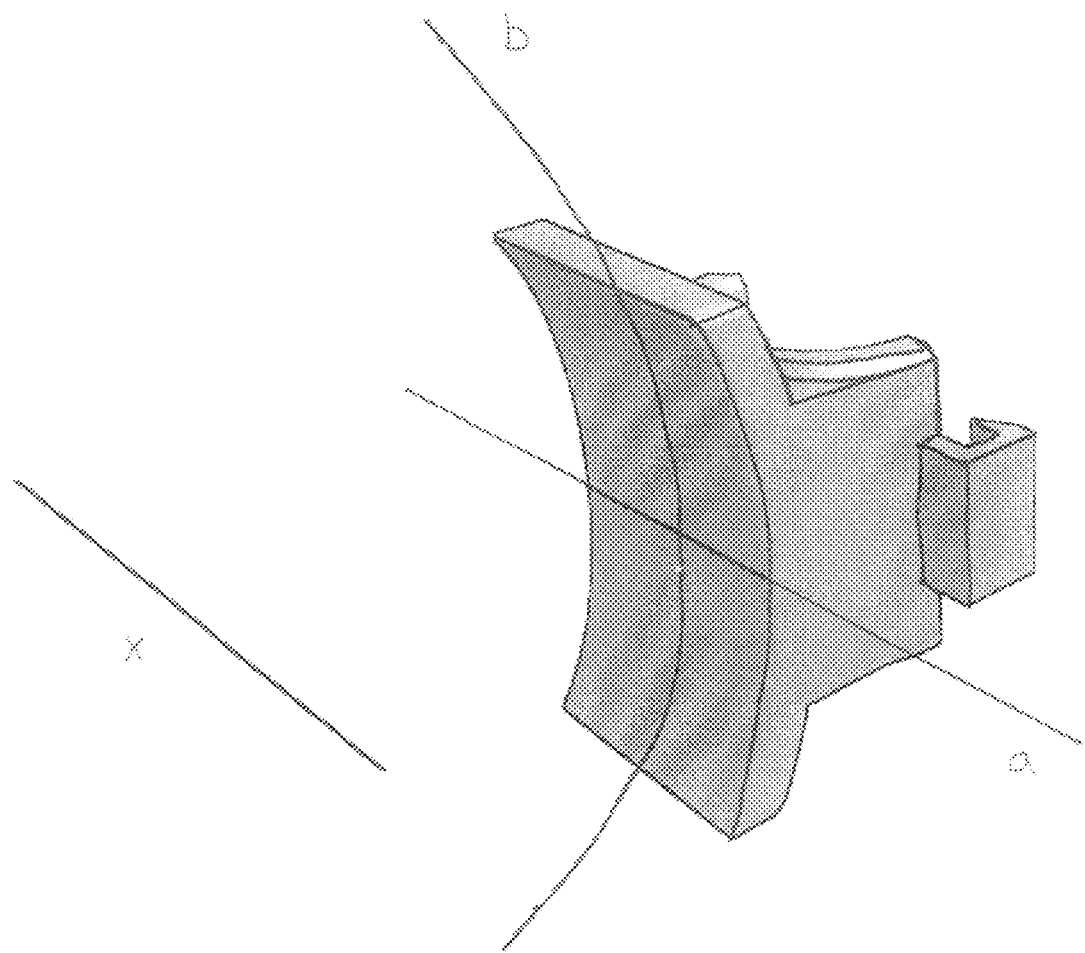
FIG. 10 is a perspective view showing the axis x and the lines of symmetry a and b.

Each clamp section 12 has a finger grip 16 located on an outer surface 18 of the clamp section 12. The outer surface 18 is positioned on the clamp section 12 opposite the semi-cylindrical surface 14. Each finger grip 16 has an arched surface 20 which includes a medial section 22 positioned between each end 24 of the finger grip 16. The ends 24 of the finger grip 16 flare away from the semi-cylindrical surface 14. The semi-cylindrical surface 14 is defined about, or has, an axis x as shown in FIG. 10.

As described in greater detail, each clamp section 12 includes a concave semi-cylindrical surface 14 which is open and unimpeded at each opposed end, thereby permitting an IV tube to extend through the cylindrical void defined by the semi-cylindrical surfaces 14. The semi-cylindrical surfaces 14 on each clamp section 12 are preferably positioned and dimensioned to mirror one another when the clamp sections 12 are secured together, so as to cooperatively define the cylindrically-shaped void between the clamp sections 12. In use, a section of an IV tube, such as a tubing port T on an IV bag, is placed within the cylindrically-shaped void and the clamp sections 12 are then secured together around the IV tube, thereby securely retaining the IV tube within the cylindrical void. The semi-cylindrical surfaces 14 are dimensioned and configured to surround and frictionally engage with the IV tube when the clamp sections 12 are secured to one another.

Figure 2:
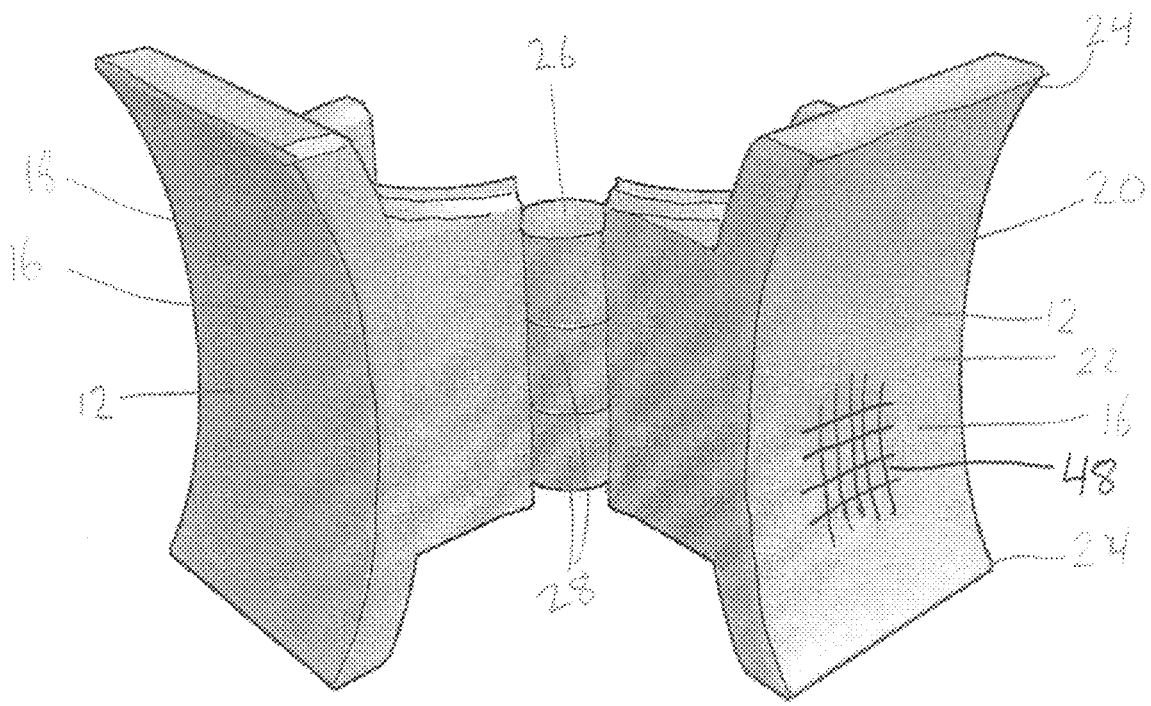
FIG. 2 is a rear perspective view hereof showing the clamp sections open with respect to one another.
Figure 4:
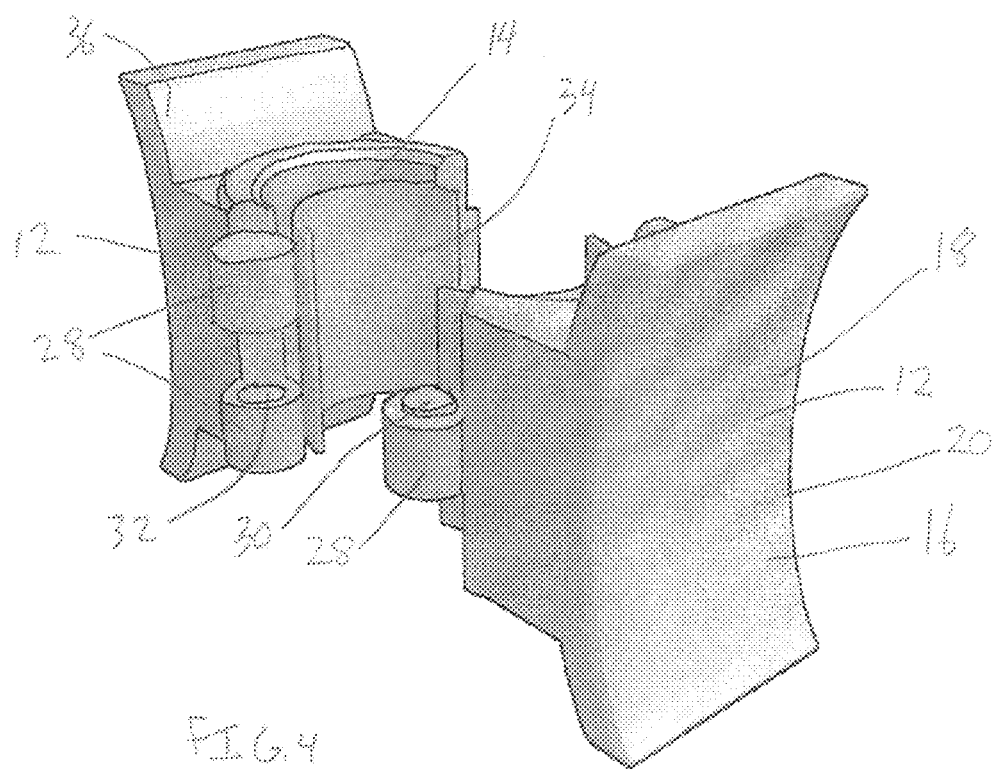
FIG. 4 is a rear exploded perspective view showing the clamp sections and lining.
Figure 5:
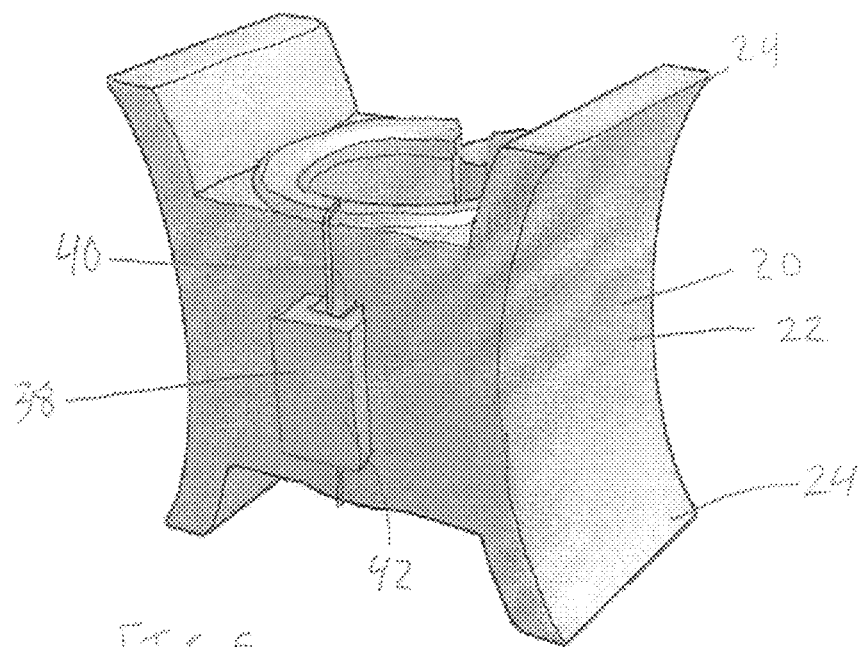
FIG. 5 is a front perspective view hereof showing the clamp sections closed with respect to one another.
Figure 6:
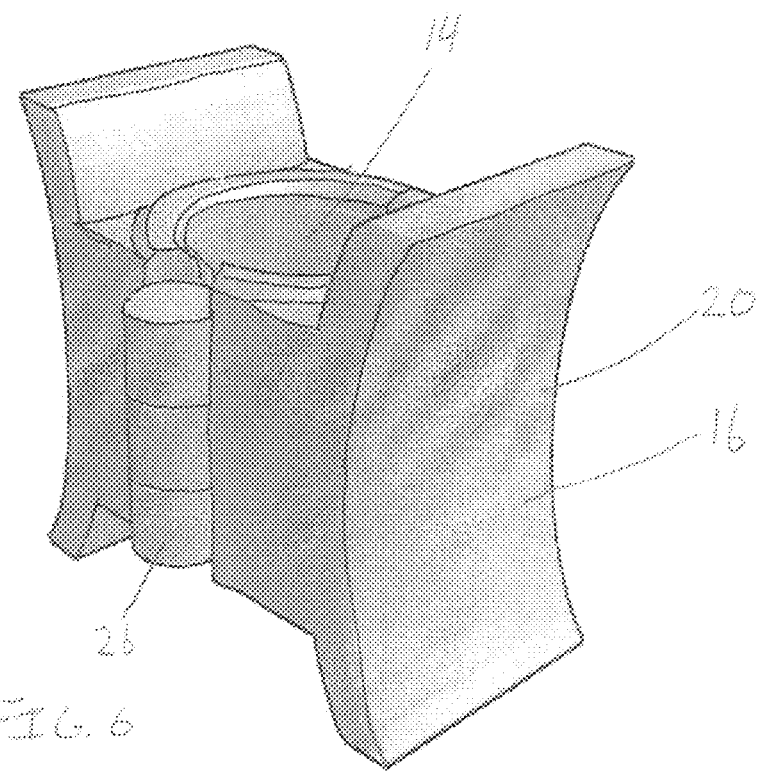
FIG. 6 is a rear perspective view hereof showing the clamp sections closed with respect to one another.
Figure 11:
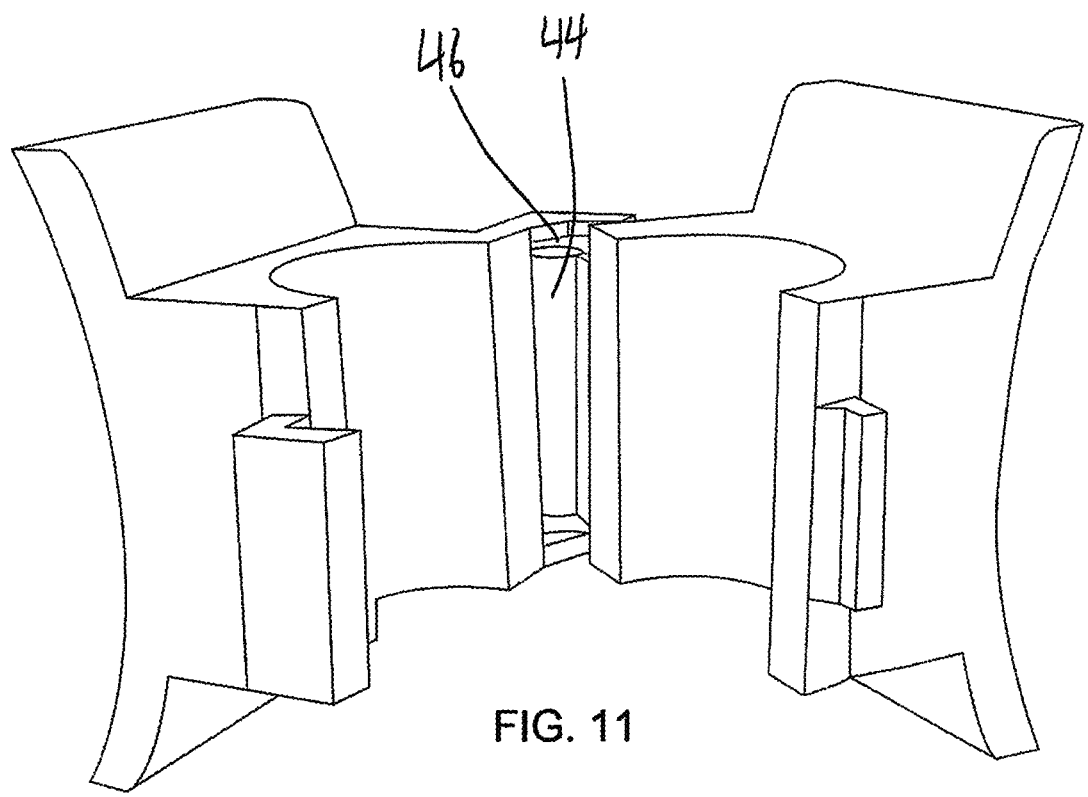
FIG. 11 shows a perspective view of open clamp sections having an alternative complementary male and female hinge.

Preferably the clamp sections 12 are hingedly secured to one another using any suitable structure or means that is well-known in the art, such as a hinge 26. For example, and as shown in FIGS. 1 and 2, the clamp sections 12 can optionally include a piano hinge that allows the clamp sections 12 to pivotally rotate with respect to one another. As understood by those having ordinary skill in the art, a piano hinge has hinge knuckles 28 which interconnect with one another. As shown in FIG. 4, the exemplary hinge knuckles 28 have respective extensions 30 and recesses 32 which rotatably engage with one another to hold the hinge knuckles 28 together. Alternatively, piano hinges are well-known to have aligned holes extending through each of the hinge knuckles 28 to permit a hinge pin to pass therethrough, such that the hinge pin rotatably secures the hinge knuckles 28 to one another. Although not shown in the drawings, another alternative possible design for the hinge 26 may be a thin flexible piece of material that is connected to each of the clamp sections 12, such as a thin bendable strip of plastic material. Another alternative hinge 26, shown in FIG. 11, includes one clamp section 12 having a cylindrical body 44 connected to a side of a first clamp section 12, and the a side of a second clamp section 12 having a complementary female portion 46 with a cylindrical void, whereby the cylindrical body 44 from the first clamp section 12 is positioned within the cylindrical void, and the clamp sections are hingedly secured to one another and can pivot along the complementary male and female cylindrical surfaces.

The clamp sections 12 can be formed from any suitable type of material that is well-known in the art, including metal, ceramic, or plastic. Preferably the clamp sections 12 are formed from an injection-moldable plastic, such as ABS, Nylon®, High Density Polyethylene, and so forth.

At least one of the semi-cylindrical surfaces 14 can have a textured surface 48 to increase friction between the semi-cylindrical surface 14 and the IV tube retained within the cylindrically-shaped void. The textured surface 48 can be embossed, knurled, or include any other suitable type of surface treatment to increase surface tension to help the clamp sections 12 engage and retain the IV tube therebetween.

Preferably, but not necessarily, at least one of the semi-cylindrical surfaces 14 has a lining 34 secured thereto. Similar to the textured surface 48, the lining 34 is provided to increase friction between the IV tube and the clamp sections 12 to assist with firmly securing the IV tube in place. The lining 34 is optionally formed from a resiliently deformable material, such as a thin and flexible foam sheet. The lining 34 functions to fill any void between the semi-cylindrical surfaces 14 and the IV tube, and also to apply additional evenly-spaced pressure around the IV tube between the clamp sections 12. The surface of the lining 34 that abuts the IV tube may optionally be sticky, or tacky, to create additional friction to hold the IV tube in place. This may be accomplished by applying an adhesive onto the surface of the lining 34, such as a pressure-sensitive adhesive. Alternatively, an adhesive may be applied directly to the semi-cylindrical surface 14 in lieu of the lining 34.

As mentioned above, each clamp section 12 has a finger grip 16 on an outer surface 18 of the clamp section 12. The finger grip 16 is positioned on the opposite side of the clamp section 12 from the semi-cylindrical surface 14. As shown throughout the drawings, it is understood that the semi-cylindrical surfaces 14 are located on an "inner" side of the clamp sections 12 when the clamp sections 12 are secured together, whereas the finger grips 16 are located on an "outer" side of the clamp sections 12 when secured together. The finger grips 16 are provided for ergonomic purposes to make it easier for a medical provider to firmly grasp the clamp 10 which is retaining an IV tube. In addition, and as described below, the finger grips 16 may also function as a shield to protect the medical provider's fingers from being accidentally pierced by the IV spike S.

As shown in the drawings, each finger grip 16 has an arched, or curved, surface 20 which includes a medial section 22 positioned between each end 24 of the finger grip 16. At least one end 24 of the finger grip 16 flares outwardly and away from the semi-cylindrical surface 14. The finger grip 16 is preferably in the form of an arc defined by an axis x as shown in FIG. 10. The finger grip 16 is also preferably symmetrical along line a, along line b, or along both lines a and b.

Optionally, the finger grip 16 may also include a finger shield 36, or shelf, which extends outwardly and beyond the semi-cylindrical surfaces 14. The finger shield 36 may be provided to increase the surface area of the finger grip 16. However, the finger shield 36 also provides a shield to protect a medical provider's fingers from being pierced by an IV spike S that has been inadvertently or accidentally positioned incorrectly while attempting to insert the IV spike S into the tubing port T.

Figure 3:
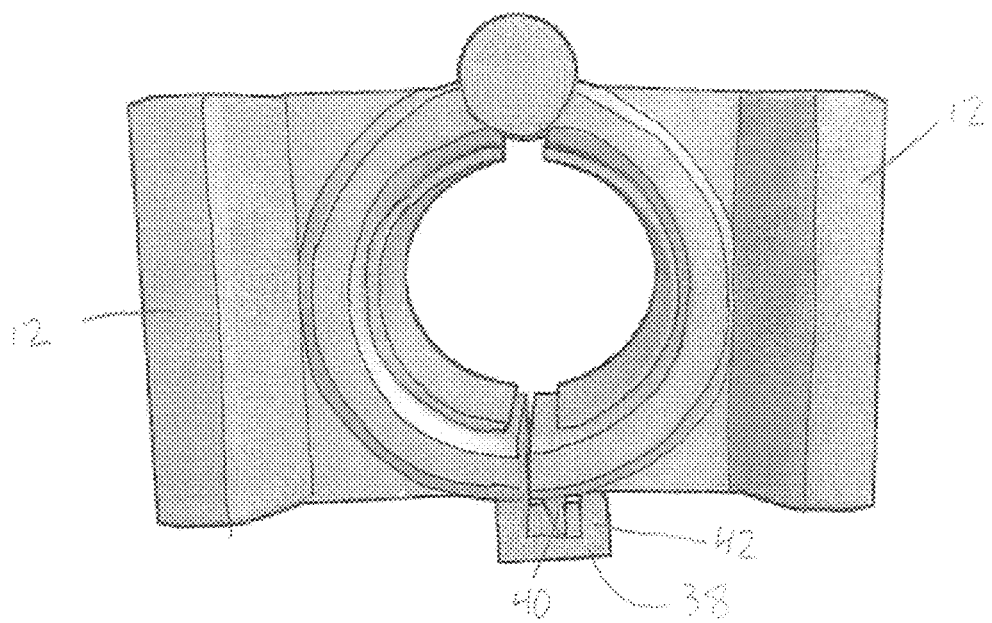
FIG. 3 is a top perspective view hereof showing the clamp sections closed with respect to one another.

As discussed above, the clamp 10 is configured to securely engage, or lock, the clamp sections 12 to one another. This may optionally be accomplished by use of a latching mechanism 38 or other hinge device which securely holds the clamp sections 12 together once a medical provider has selectively engaged the clamp sections 12 together. One example of a latching mechanism 38 is shown best in FIGS. 1 and 3, wherein one of the clamp sections 12 has a tab 40 extending off the side thereof, and the other one of the clamp sections 12 has a "L"-shaped catch 42 extending off the side thereof, and as shown in FIG. 3 the tab 40 and the catch 42 are positioned such that the catch 42 retains the tab 40, thereby securing the two clamp sections 12 together. Alternatively, each clamp section 12 can have complementary male and female connectors with one side of each clamp section 12 having the male connector and the other side have the female connector, and whereby the mated male and female connectors on each clamp section 12 are aligned and snapped together.

Figure 7:
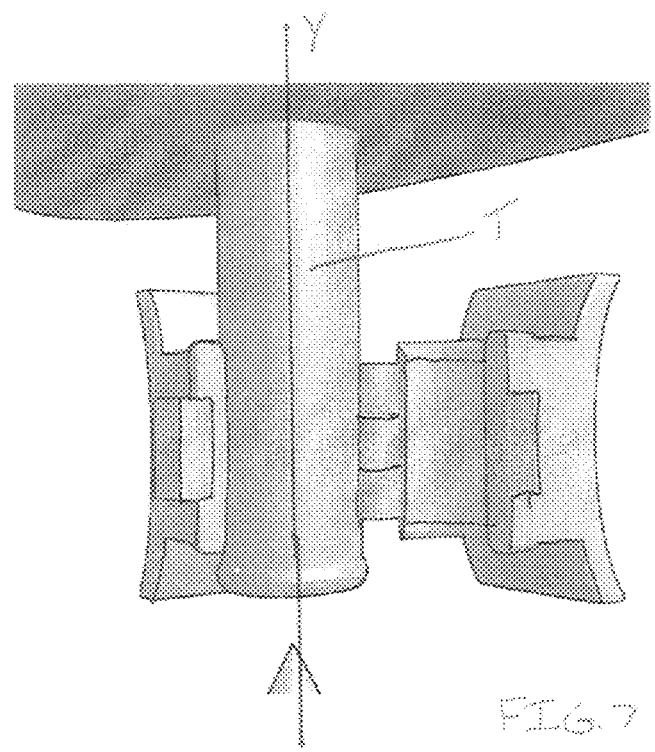
FIG. 7 is an environmental view showing the clamp sections open with respect to one another, and a tubing port from an IV bag positioned adjacent the semi-cylindrical surface on one of clamp sections.
Figure 8:
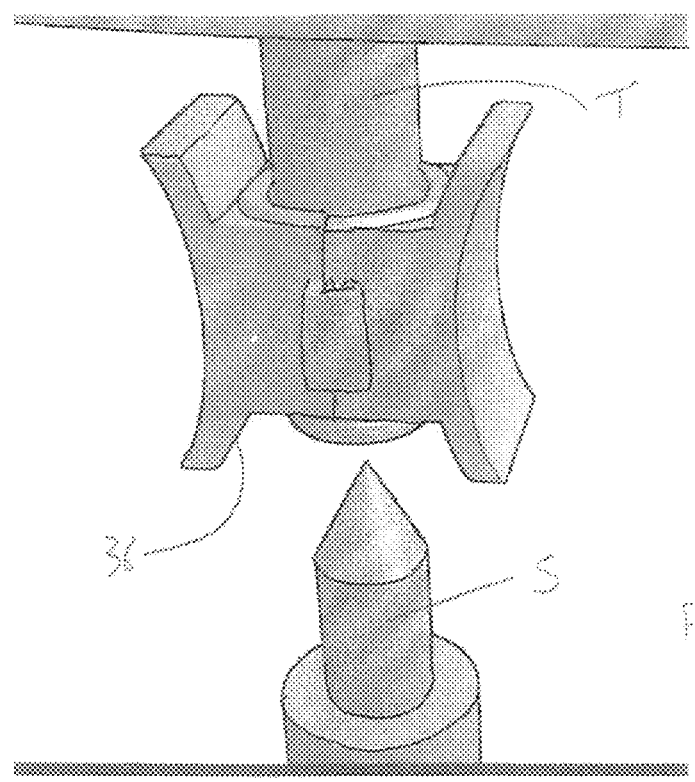
FIG. 8 is an environmental view showing the clamp sections closed with respect to one another, and a tubing port from an IV bag positioned within the cylindrical void, and the IV spike positioned below the tubing port and clamp prior to insertion of the IV spike into the tubing port.
Figure 9:
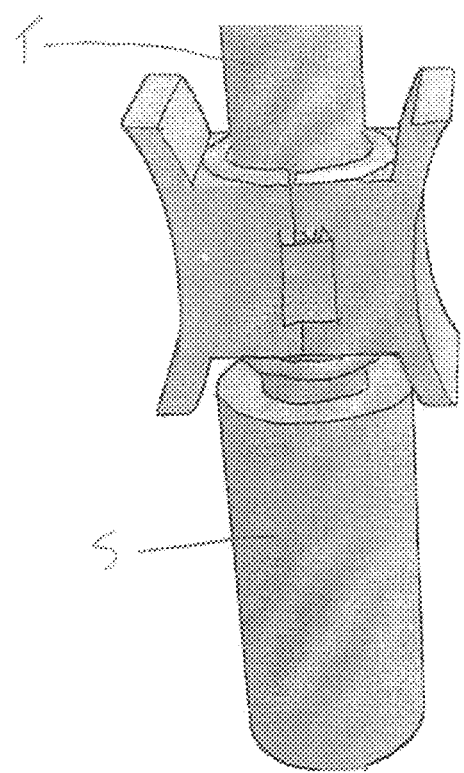
FIG. 9 is an environmental view similar to FIG. 8, but showing the IV spike inserted into the tubing port.

Preferably, the axis y for each semi-cylindrical surface 14 (as seen in FIG. 7) is oriented perpendicular to the axis x of the finger grip 16 on the same respective clamp sections 12. This orientation of the semi-cylindrical surfaces 14 with respect to the finger grips 16 facilitates the medical provider in grasping the clamp 10 (which retains the tubing port T) in one hand, while the other hand manipulates and forces the IV spike S through the membrane of the tubing port T. In addition, the finger grips 16 being oriented in this manner also provide a shield to protect the medical provider's fingers holding the clamp 10 if the medical provider inadvertently misaligns the IV spike S with the tubing port T.

According to the invention described above, a device is provided which allows a medical provider to securely and safely grasp the tubing port on an IV bag to assist with safely inserting an IV spike therein.

It should be understood that the foregoing description is only illustrative of the aspects of the disclosed embodiments. Various alternatives and modifications can be devised by those skilled in the art without departing from the aspects of the disclosed embodiments. Accordingly, the aspects of the disclosed embodiments are intended to embrace all such alternatives, modifications, and variances that fall within the scope of the appended claims. Further, the mere fact that different features are recited in mutually different dependent or independent claims does not indicate that a combination of these features cannot be advantageously used, such as a combination remaining within the scope of the aspects of the disclosed embodiments.

What is claimed is:

1. A clamp for retaining an IV tube comprising:
a pair of clamp sections that are configured to be selectively secured to one another, each clamp section includes a semi-cylindrical surface, and the semi-cylindrical surfaces are positioned to mirror one another when the clamp sections are secured together, wherein the semi-cylindrical surfaces cooperatively define a cylindrical void between the clamp sections, and the semi-cylindrical surfaces are configured to surround and frictionally engage with the IV tube when the clamp sections are secured together; and
each clamp section having a finger grip on an outer surface of the clamp section, the outer surface being positioned on an opposite side of the clamp section from the semi-cylindrical surface, each finger grip having an arched surface which includes a medial portion positioned between each end of the finger grips, and at least one end of the finger grip flares away from the semi-cylindrical surface; and
wherein the semi-cylindrical surface of at least one of the clamp sections has an axis y, and the arched surface of the finger grip of that clamp section has an axis x, wherein the axis y and the axis x are oriented perpendicular to one another.

2. The clamp of claim 1 wherein the clamp sections are hingedly secured to one another.

3. The clamp of claim 1 wherein at least one of the semi-cylindrical surfaces includes a resiliently deformable lining to help secure the IV tube between the clamp sections.

4. The clamp of claim 1 wherein at least one of the semi-cylindrical surfaces includes a lining having an adhesive to help secure the IV tube between the clamp sections.

5. The clamp of claim 1 wherein at least one of the semi-cylindrical surfaces has a textured surface to help secure the IV tube between the clamp sections.

6. The clamp of claim 1 wherein the clamp sections are hingedly connected to one another, and the clamp includes a latch mechanism having a catch connected to one of the clamp sections, and a complementary tab connected to the other clamp section.

7. The clamp of claim 1 wherein the clamp sections are hingedly connected to one another, and the clamp includes a latch mechanism having a catch connected to one of the clamp sections, and a complementary tab connected to the other clamp section.

8. A clamp for retaining an IV tube comprising:
a pair of clamp sections that are configured to be selectively secured to one another, each clamp section includes a semi-cylindrical surface, and the semi-cylindrical surfaces are positioned to mirror one another when the clamp sections are secured together, wherein the semi-cylindrical surfaces cooperatively define a cylindrical void between the clamp sections, and the semi-cylindrical surfaces are configured to surround and frictionally engage with the IV tube when the clamp sections are secured together; and
each clamp section having a finger grip on an outer surface of the clamp section, the outer surface being positioned on an opposite side of the clamp section from the semi-cylindrical surface, each finger grip having an arched surface which includes a medial portion positioned between each end of the finger grips, and at least one end of the finger grip flares away from the semi-cylindrical surface and at least one of the finger grips is symmetrical; and
wherein the semi-cylindrical surface of at least one of the clamp sections has an axis y, and the arched surface of the finger grip of that clamp section has an axis x, wherein the axis y and the axis x are oriented perpendicular to one another.

9. The clamp of claim 8 wherein the clamp sections are hingedly secured to one another.

10. The clamp of claim 8 wherein at least one of the semi-cylindrical surfaces includes a resiliently deformable lining to help secure the IV tube between the clamp sections.

11. The clamp of claim 8 wherein at least one of the semi-cylindrical surfaces includes a lining having an adhesive to help secure the IV tube between the clamp sections.

12. The clamp of claim 8 wherein at least one of the semi-cylindrical surfaces has a textured surface to help secure the IV tube between the clamp sections.

13. The clamp of claim 8 wherein the clamp sections are hingedly connected to one another, and the clamp includes a latch mechanism having a catch connected to one of the clamp sections, and a complementary tab connected to the other clamp section.

14. The clamp of claim 8 wherein at least one of the finger grips is symmetrical.

15. A clamp for retaining an IV tube comprising:
a pair of clamp sections that are configured to be selectively secured to one another, each clamp section includes a semi-cylindrical surface, and the semi-cylindrical surfaces are positioned to mirror one another when the clamp sections are secured together, wherein the semi-cylindrical surfaces cooperatively define a cylindrical void between the clamp sections, and the semi-cylindrical surfaces are configured to surround and frictionally engage with the IV tube when the clamp sections are secured together; and
each clamp section having a finger grip on an outer surface of the clamp section, the outer surface being positioned on an opposite side of the clamp section from the semi-cylindrical surface, each finger grip having an arched surface which includes a medial portion positioned between each end of the finger grips, and at least one end of the finger grip flares away from the semi-cylindrical surface; at least one of the ends of each finger grip includes a finger shield which extends laterally beyond the semi-cylindrical surface; and
wherein the semi-cylindrical surface of at least one of the clamp sections has an axis y, and the arched surface of the finger grip of that clamp section has an axis x, wherein the axis y and the axis x are oriented perpendicular to one another.

* * * * *